United States Patent [19]

Dupain et al.

[11] Patent Number: 4,849,175
[45] Date of Patent: Jul. 18, 1989

[54] APPARATUS FOR AUTOMATICALLY DETERMINING CERTAIN CHARACTERISTICS OF CEMENT

[75] Inventors: Jean R. Dupain, St. Maur; Christian P. Vernet, Jouy-Mauvoisin, both of France

[73] Assignee: Societe Des Ciments Francais, France

[21] Appl. No.: 140,965

[22] Filed: Jan. 4, 1988

Related U.S. Application Data

[63] Continuation of Ser. No. 733,216, May 10, 1985, abandoned.

[30] Foreign Application Priority Data

May 16, 1984 [FR] France ............................... 84 07560

[51] Int. Cl.⁴ ............................................ G01N 35/00
[52] U.S. Cl. .................................. 422/63; 141/83; 141/103; 177/50; 177/52; 177/54; 177/55; 414/21; 414/180; 414/186; 422/64; 422/68; 422/75; 422/78; 422/104
[58] Field of Search ........................ 422/63–65, 422/67, 68, 75, 78, 104; 177/50, 52, 54, 55, 150; 141/83, 103; 414/21, 180, 186

[56] References Cited

U.S. PATENT DOCUMENTS

| | | | |
|---|---|---|---|
| 3,870,465 | 3/1975 | Maréchal | 422/68 |
| 4,113,436 | 9/1978 | Werder et al. | 422/65 |
| 4,391,774 | 7/1983 | Dupain | 422/63 |
| 4,562,044 | 12/1985 | Bohl | 422/63 |
| 4,595,562 | 6/1986 | Liston et al. | 422/64 |

*Primary Examiner*—Michael S. Marcus
*Assistant Examiner*—Amalia L. Santiago
*Attorney, Agent, or Firm*—Darby & Darby

[57] ABSTRACT

A method and apparatus for automatically measuring the grain fineness, the gypsum content and the limestone content of a cement sample.

A first fraction of the sample is loaded by a vibrating hopper into a crucible resting on an automatic scale. This crucible is handled sequentially by tongs on two revolving arms carried on slidable vertical shafts. The circular paths of the arms intersect at a point just above the scale. Motions of the arms and of the tongs are controlled by a programming unit. The weighed sample is poured into a sieve and the weight of oversize grains is automatically related to the sample weight.

Gypsum is measured by heating a second fraction of the sample at 1000° C. plus in an oxygen stream, Fe powder being added from a fixed hopper. The crucible is raised into an induction furnace. Released $SO_2$ is bubbled in a titration cell to which potassium iodate is gradually added by a burette giving an automatic read-out of the $SO_3$ (gypsum) titration.

Limestone is also measured by heating a third fraction of the sample to release $CO_2$, and measuring the weight increase of a column, filled with NaOH which absorbs the released $CO_2$, which is placed on a second automatic scale. The column is automatically disconnected from the gas circuit before being weighed.

15 Claims, 6 Drawing Sheets

APPARATUS FOR AUTOMATICALLY DETERMINING CERTAIN CHARACTERISTICS OF CEMENT

This is a continuation of co-pending application Ser. No. 733,216, filed on May 10, 1985, now abandoned.

This invention relates to a method and apparatus for automatically determining certain characteristics of cements, namely grain fineness, the proportion of gypsum and the proportion of limestone filler.

BACKGROUND OF THE INVENTION

U.S. Pat. No. 4,391,774, granted July 5,1983, which corresponds to French Patent Application No. 80.14302 filed on June 27, 1980, describes an apparatus for analyzing samples of the raw mix being fed to a cement kiln. This apparatus is designed for automatically producing vitrified samples called "pearls" which will subsequently be analyzed by an X-ray spectrometer. This apparatus comprises a swivelling arm carrying tongs for handling a crucible, in combination with a weighing system and a furnace. Using this apparatus, it is possible to obtain automatically and rapidly an analysis of the components of the raw mix being fed to a cement kiln. However, after the cement has left the kiln and after the clinker has been crushed, there remains the need to add to this clinker additives such as gypsum and limestone filler. There is also the need to monitor the regularity of the grain size distribution of the finished cement.

SUMMARY OF THE INVENTION

The present invention relates to a method and apparatus for automatically carrying out a measurement of the grain fineness of a cement sample, together with a measurement of the sulfur trioxide ($SO_3$) content of this sample for providing a determination of the gypsum content, and a measurement of the carbon dioxide ($CO_2$) content of the sample for providing a determination of the proportion of limestone filler.

The method of this invention for measuring the grain fineness of a cement sample comprises carrying out automatically, in sequence, the following operations:
 weighing a fraction of the sample,
 placing this fraction on a sieve,
 running water through the sieve,
 drying the sieve,
 cooling down the sieve,
 weighing the sieve with the oversize material,
 emptying, washing, drying and cooling down the emptied sieve,
 weighing the emptied sieve.

The comparison of the results from these three weighings will indicate the weight of oversize material as related to the sample weight.

According to a preferred embodiment, the weighing results obtained with a series of samples are memorized for providing an indication of the gradual clogging of the sieve and giving a warning when the sieve needs to be replaced.

The method of the invention further comprises carrying out sequentially and automatically the following operations for measuring the $SO_3$ content of the same cement sample being analyzed for grain size:
 placing a suitable amount of iron powder in the bottom of a crucible made of alumina,
 weighing a fraction of the sample which fraction is in the alumina crucible on top of the iron powder,
 placing a quartz wool plug on the crucible,
 transferring the crucible into an induction furnace,
 sweeping over the furnace with a high-flow oxygen stream,
 measuring the $SO_3$ content by iodometry for determining the gypsum content of the sample,
 removing the crucible from the furnace,
 discarding the used crucible.

A third series of steps in the method of this invention comprises automatically carrying out in sequence the following operations for measuring the $CO_2$ content of the same sample of cement:
 weighing a fraction of the sample placed in a platinum crucible,
 weighing a $CO_2$ trap filled with sodium hydroxide (soda) granules,
 transferring the platinum crucible into an induction furnace,
 sweeping over the furnace with a moderate flow of oxygen,
 allowing the $CO_2$ to be trapped by the soda granules in the $CO_2$ trap,
 weighing the $CO_2$ trap including the trapped $CO_2$.

These operations will provide a precise indication of the limestone content of the cement.

This invention further provides an automatic apparatus for carrying out the measurements of grain fineness, gypsum content and limestone filler content of a cement sample.

This apparatus comprises:
 two swivelling arms with tongs for holding a crucible, the circular paths of which arms intersect above an automatic weighing scale,
 one vibratory hopper, the mobile spout of which is adapted for discharging into a container placed on the tray of the weighing scale,
 one fixed hopper, magnetically closed, situated above the weighing scale,
 a measuring assembly for measuring physiochemical characteristics, said assembly comprising an induction furnace associated with the first swivelling arm, and
 a water-jet assisted sieve assembly associated with the second of the two swivelling arms.

Preferably, this apparatus will comprise two hoppers one of them being vibratory and equipped with mobile spout, while the sieve assembly will comprise means for injecting drying or cleaning agents and means for drying a sieve. The measuring assembly for measuring physiochemical characteristics comprises a source of vector gas, a $CO_2$ trap, and an automatic beaker such as the one described in a French Patent Application No. 84.07561, filed on May 16, 1984 by Applicant, now abandoned. This beaker provides for measuring the $SO_3$ content by means of the iodometric method using potassium iodate.

BRIEF DESCRIPTION OF THE DRAWINGS

The apparatus of this invention will now be described in detail, with reference to appended drawings which show, by way of non-limitative example for an easier understanding of the invention, one embodiment of this apparatus, in which.

DETAILED DESCRIPTION OF THE INVENTION

Figure 1:
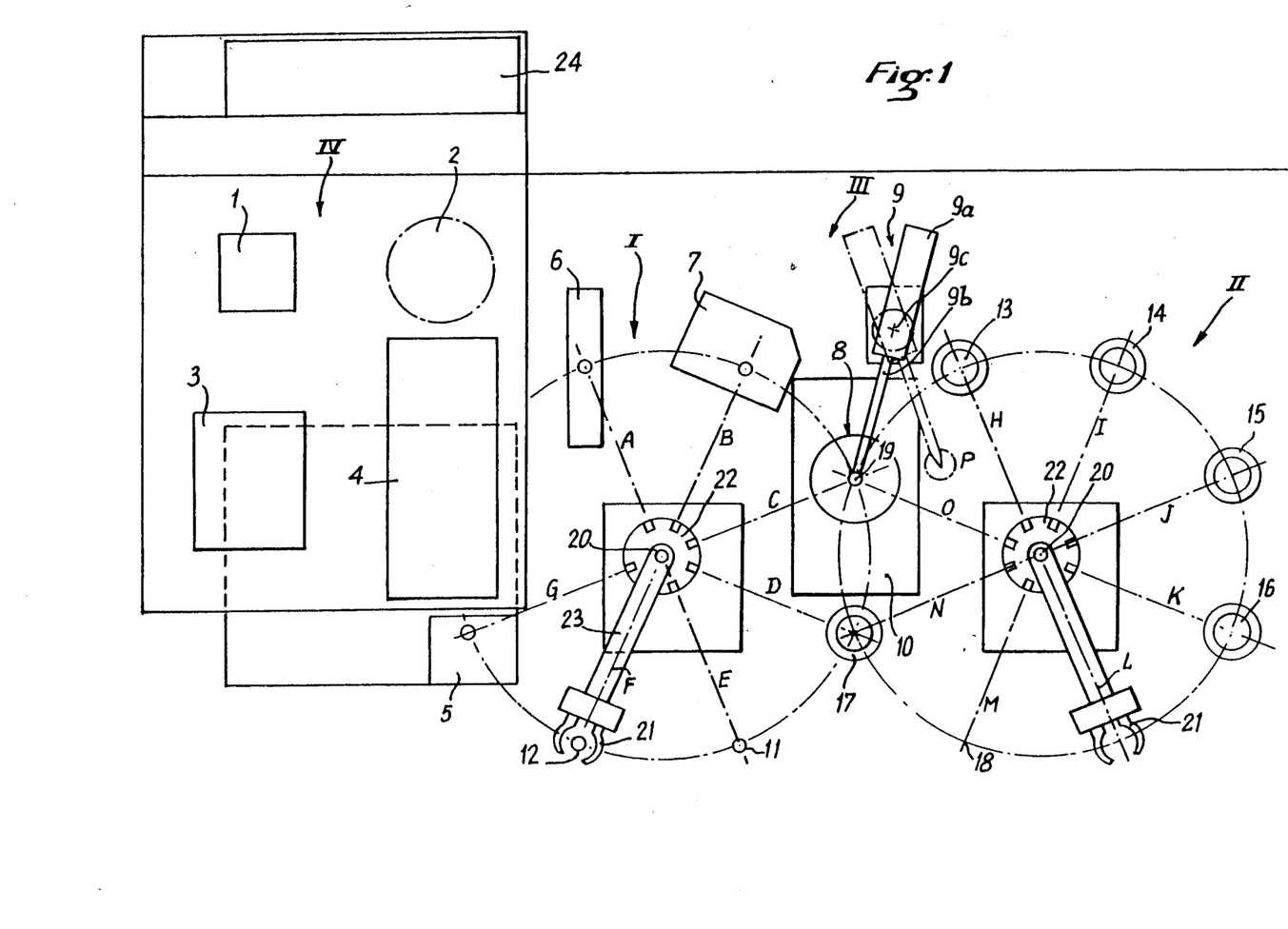
FIG. 1 is a diagrammatic aerial view showing the elements of the apparatus and their various positions.

Referring to FIG. 1, it will be seen that the apparatus of this invention comprises:

a weighing assembly III comprising a weighing scale 10 associated with two feed hoppers 8 and 9, a distribution assembly I and II comprising two swivelling arms 23, the first arm being adapted for leading into seven stations (A through G), the second arm being adapted for leading into seven stations (I through 0), while the circular paths of these two arms intersect, one of their two intersection points 19 being located vertically above the scale 10 of the weighing assembly III, and a measuring assembly IV for measuring physiochemical characteristics, comprising a furnace served by the first arm.

Here, the swivelling arms will not be described in detail, as they are of a known type, an example of such an arm being described in U.S. Pat. No. 4,391,774 referred to above. It is noted that each arm is mounted on a vertical shaft 20 linked to a jack so as to be raised or lowered, each horizontal arm 23 being provided on its end with tongs 21 for taking hold of a crucible or any cylindrical object and being adapted for rotating 180° about its longitudinal axis, the mechanical drive for rotating the vertical shaft 20 being provided with means 22 for immobilizing it in any one of a plurality of predetermined positions.

The first swivelling arm 23 which serves the distribution assembly I may be immobilized by means 22 in any of seven different positions referenced A through G. In position A is provided a mechanical system 6 for distributing quartz wool plugs for sealing certain crucibles. In position B is provided a magazine or distributor 7 for dispensing alumina crucibles. In position C is an automatic scale 10, under the intersection point 19 of the paths of the two swivelling arms 23. In position D is found the second intersection point 17 of these paths. Position E is a waiting or storage station of point 11 in which is located the platinum crucible, while position F corresponds to a draining orifice at point 12, and position G corresponds to the insertion of the crucible being handled (a platinum or alumina crucible according to the specific cases) into the induction furnace 5 of the measuring assembly IV.

The second swivelling arm 23 which serves the distribution assembly II may be immobilized in any of seven different positions I through O.

Position I corresponds to a heating device at point 14 used for drying the sieve, which will be described hereinafter with reference to FIG. 7. In position J at point 15, the sieve is tipped over 180° for being cleared by washing of the grains retained in the sieving operation. In position K at point 16 is a pressurized water nozzle (ca. 1 kg/cm²) for carrying out the sieving operation. Position L is a second drying position of the second arm 23. Position M corresponds to a storage station at point 18 for the sieve when it is too dirty and to a waiting station for a second clean sieve. Position N corresponds to the second intersection point 17 of the paths of the arms and to the sieve cooling position, while position 0 corresponds to the first intersection point 19 of the paths and to the automatic weighing scale 10.

The weighing assembly III comprises a first hopper 8 situated above the hood 25 of the weighing scale 10, a second vibratory hopper 9 and the automatic scale 10.

The above part of weighing scale 10 is protected by a hood 25. This hood is displaced vertically by a jack (not shown) in order to allow spout 9b of vibratory hopper 9 to come into position. Said spout 9b goes through an aperture managed in the back side of said hood 25. The upper face of said hood 25 is supporting hopper 8.

The vibratory hopper 9 is not described in detail, since it is similar to the one described in the above-mentioned U.S. Pat. No. 4,391,774. It is both formed of a hopper as such 9a, having an extension in the form of a spout with a V-shaped section, 9b. Discharge is carried by a mechanical device which can be vibrated and the spout 9b is slightly slanted so that, when the hopper and its spout are vibrated, the powder contained in the hopper will flow out slowly and regularly.

Figures 6, 8:
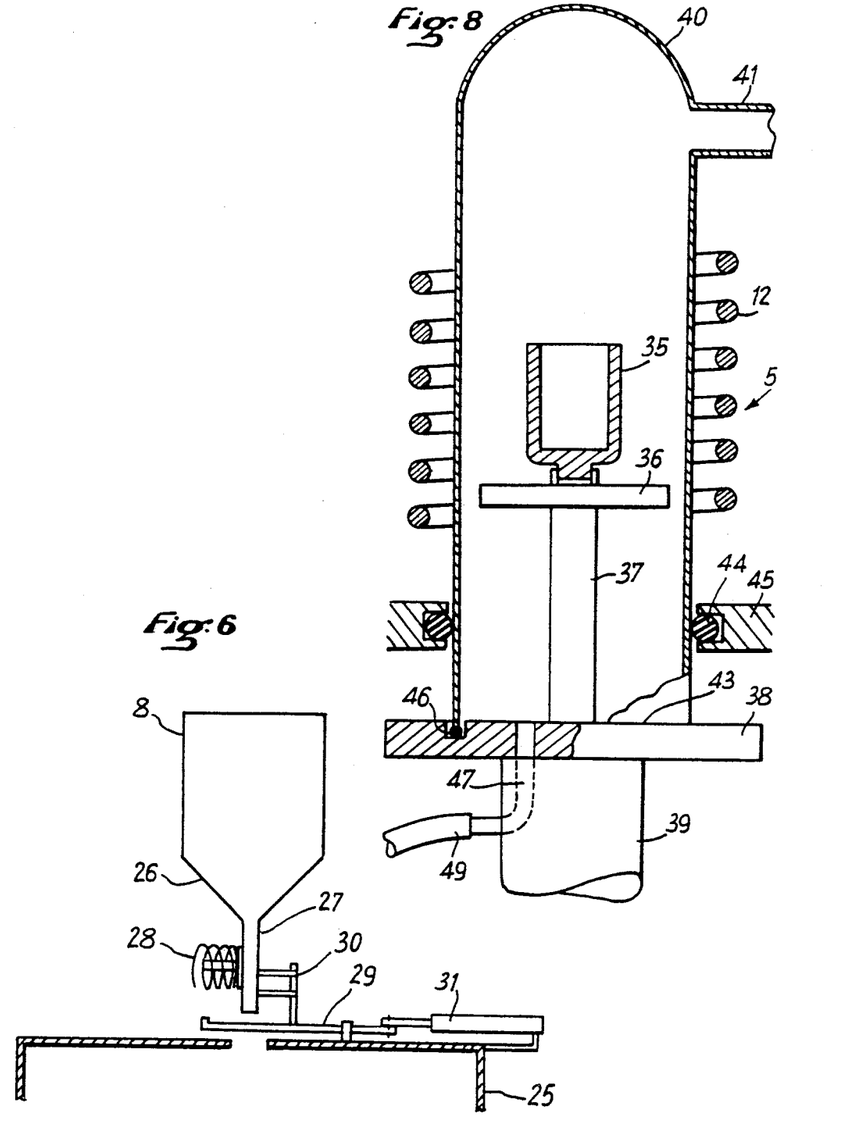
FIG. 6 is a diagrammatic partially cut-out side elevation view of a hopper placed above the weighing scale, with a magnetic closure.
FIG. 8 is a diagrammatic view showing a crucible placed inside the induction furnace.

Hopper 8, as shown in FIG. 6, is carried above protecting hood 25 of weighing scale 10. Its purpose is to realize addition of iron powder when measuring the $SO_3$ content. Said hopper 8 comprises a funnel 26 at the base of which is a tubular duct 27 which is right above the crucible when the latter comes into the weighing position. On the side of duct 27 is situated an electrical magnet 28, which, when energized, blocks the flow of powder iron inside the duct 27. When weighing the amount of powder iron, electrical magnet 28 is de-energized at high frequency, which allows the powder iron to pour down. As a safety device, in order to prevent any undue flow of powder iron into the crucible when the pouring is stopped, a mechanical shutter 29 and a magnetic shutter 30 made of a permanent magnet are brought in place with one, shutter 29, below the mouth of duct 27 and the other one, shutter 30, on the side of duct 27 by means of a single acting jack 31.

Hopper 9 is carried by means allowing it to revolve about axis 9c from a first position in which the output of spout 9b is at point 19 and a second offset position, shown in dotted lines, in which spout 9b is turned aside from the scale 10 so that the outlet will rest over a draining orifice P for emptying the hopper at the end of a cycle and for rinsing said hopper.

The above-described apparatus is designed for automatically carrying out the three following measurements on one same sample of cement:

measurement of the fineness of the cement grains, that is a grain-size measurement, measurement of the gypsum content, by measuring the $SO_3$ content, measurement of the lime filler content, by measuring the $CO_2$ content.

1. Measurement of Grain Fineness

Figure 2:
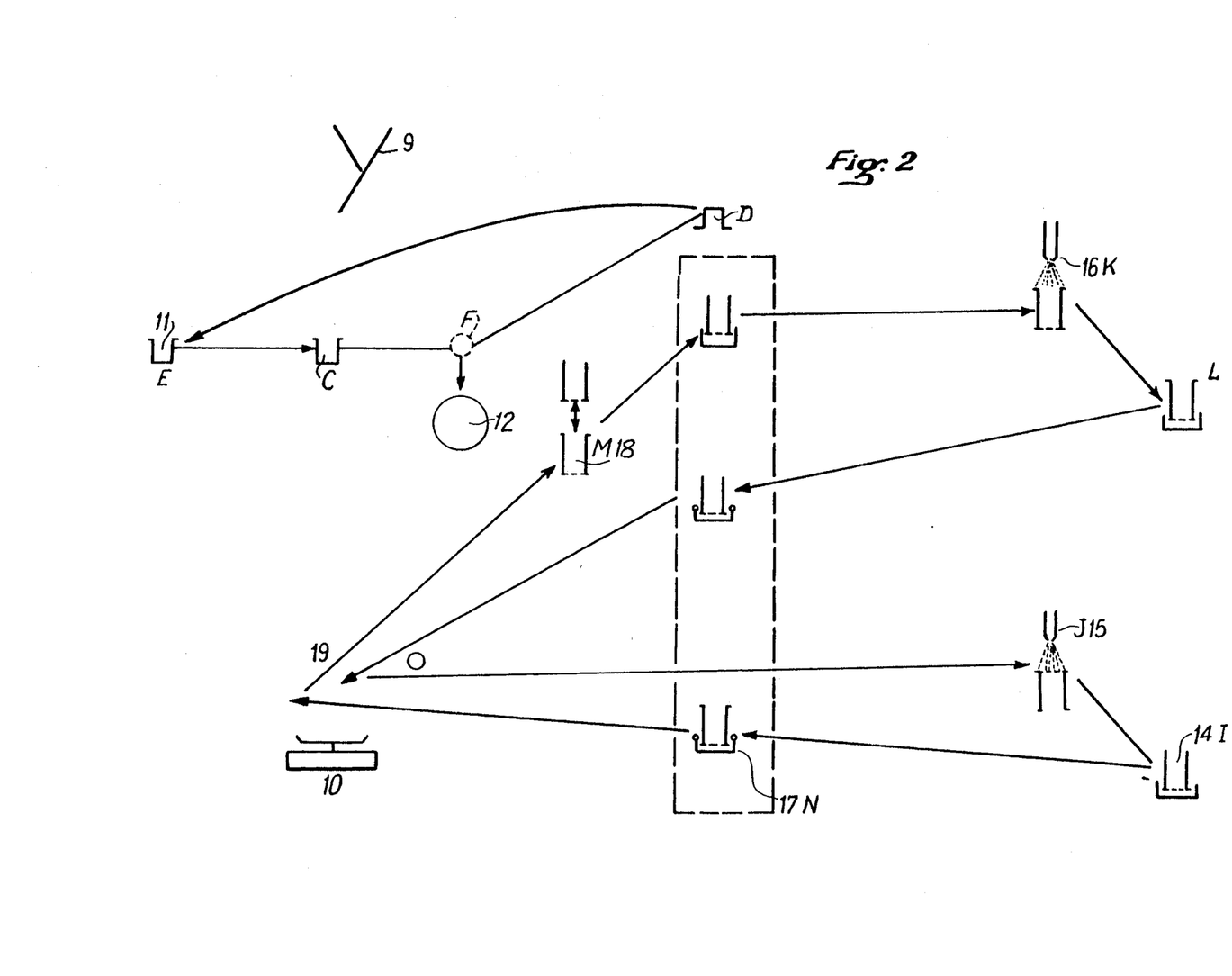
FIG. 2 is a diagram illustrating the various sequential steps of the grain fineness measurement.

Operations progress sequentially and automatically in the order described hereinafter, a graphic illustration of which is shown in FIG. 2. In this cycle, the two swivelling arms 23 operate one after the other. FIG. 2 is labelled "start" corresponding to the following descriptions.

The first arm 23 of distribution system 1 is brought by a programming unit 24 into position E and the tongs 21 grasp a platinum crucible from its waiting position at point 11. The arm 23 is then rotated clockwise to position C corresponding to point 19, where the tongs release the crucible which is deposited on the scale 10. Hood 25 is raised and hopper 9 is then rotated so that the tip of spout 9b comes above point 19, that is above the crucible; hood 25 is then lowered. At each weighing operation the steps of putting the crucible in place, of putting the sieve in place, and/or of bring the extremity of the spout to above the crucible is preceded by raising the hood 25 and followed by lowering said hood 25 to its original position. The hopper 9 is then vibrated and cement flows through spout 9b into the crucible, and scale 10 does the weighing. When the predetermined weight is attained, the scale 10 sends out a stop signal to the programming unit 24 which stops the vibration of hopper 9 and thus the flow of cement out of the hopper 9. The flow of cement may not be interrupted at once, therefore the weighing error may exceed a margin set in advance and stored in the memory of the programming unit 24. In such a case, this unit 24 will cause arm 23 to rotate into position F and the tongs to tip 180° for emptying the crucible into the draining orifice at point 12. The arm 23 is then reverted to position C at point 19 for making another weighing. If this time the weight is correct, arm 23 will be rotated to position D overlying a sieve resting in a waiting position at point 17. The tongs will be tipped 180°, then brought back to their original position and tipped again so that the crucible empties into the sieve at point 17. The arm 23 is then reverted to position E.

Arm 23 of distribution system II is then activated by the programming unit 24 and brought to position N, where its tongs 21 pick up the sieve which has just been filled and is at point 17. Arm 23 moves further to position K, so as to bring the sieve to point 16. At this point 16 is provided a cleaning device which sends our pressurized water into the sieve while rotating said sieve so as to stir the cement and to propel through the sieve those grains being smaller than the sieve mesh.

Figure 7:
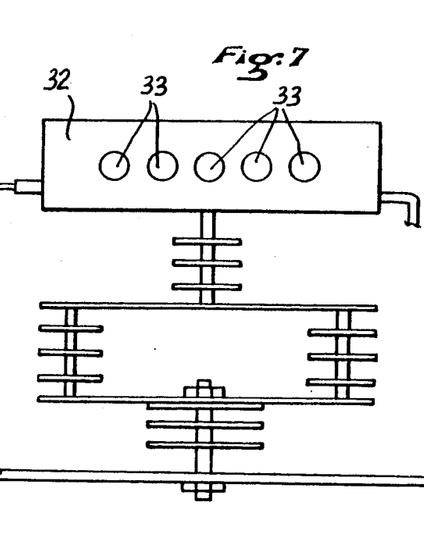
FIG. 7 is a diagrammatic cut-out side elevation of a heating plate.

Arm 23 is then rotated to position L so as to bring the sieve above a drying device, details of which are shown in FIG. 7. The drying device 14, similar to the drying device of position I at point 14, and as shown in FIG. 7, comprises a heating plate 32 controlled by a thermostat. On the base of said plate 32 are provided a plurality of air circulating holes 33. When drying is achieved, arm 23 is brought into position N at point 17 in order to bring the sieve in the middle of a cooling device. Said cooling device (not shown) is made of a circular tubing having a plurality of apertures on its lower side through which compressed air is blown over the sieve resting on a water cooled plate. The arm 23 is rotated by programming unit 24 to position O where the sieve is at point 19 on weighing scale 10.

The tongs 21 release the sieve which is then weighed, its weight being recorded in the programming unit 24. Thus is obtained the total weight of the sieve plus the oversize grains. The sieve is then picked up again by the tongs 21 and brought to point 15 as the arm reaches position J. At this point, the tongs are tipped 180° and the sieve is cleaned by a water jet. Arm 23 is then rotated along its longitudinal axis so that the sieve is tipped over, cleaned, tipped back and cleaned again. A cleaning and a drying agent may be added. Then arm 23 goes to position I where sieve is dried at point 14 by a drying device similar to the one at position L described above, and goes to position N where the sieve is cooled. Following this, arm II reverts to position O where the sieve is released at point 19 on the scale for making a further weighing. The difference between the two weighings indicates the weight of oversize grains. A further feature is that a comparison is made of the third weighings of each cycle for measuring the gradual clogging of the sieve, so that it may be discarded in position M at point 18, and replaced by a new one, when the clogging exceeds a predetermined amount.

The weight of oversize material is compared with the weight of cement poured into the sieve at the beginning of the cycle, and the oversize fraction is then expressed as a percentage.

2. Measurement of the gypsum content

This measurement is made by measuring the total sulfur content of the sample by means of a known method in which the product is heated above 1,000° C. and a determination is made of the total sulfur content of the vapors released from the furnace by bubbling them through a bath, the potential of which is kept constant by adding potassium iodate.

It has proved necessary to use a stream of vector gas for carrying the gases released from the furnace into the bubbling bath. This vector gas is oxygen. If cement is heated without added oxygen, there is a risk that sulfur present in the cement will be incompletely released.

For this operation, use is made, in known fashion, of alumina crucibles which are discarded after each use. Since alumina is not electroconductive, it is necessary to pour into the crucible a certain amount of iron powder for making induction heating possible. This has the further advantage that iron will act as a regulating agent in the reaction.

Figure 3:
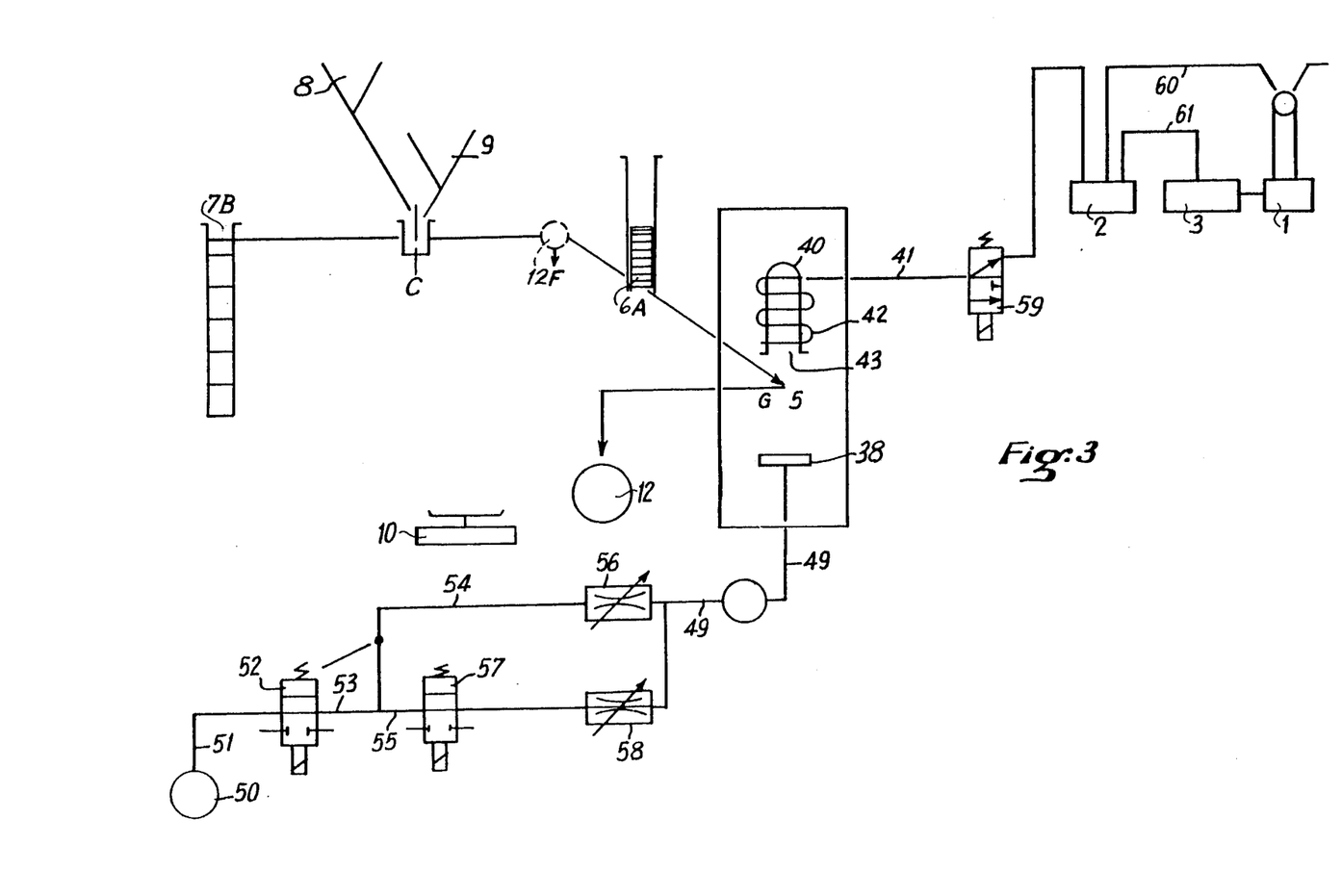
FIG. 3 is a diagram similar to the one of FIG. 2, showing the sequential steps of the $SO_3$ content measurement.

The cycle of this measurement is illustrated diagrammatically in FIG. 3.

Swivelling arm 23 of distribution system I is rotated, under control by the programming unit 24, to position B where the tongs 21 pick up an alumina crucible from a magazine 7. Next, the arm 23 moves to position C and releases the crucible at point 19 on the scale 10. Hopper 9 is rotated so that the tip of its spout 9b comes vertically above point 19. The alumina crucible is weighed. Then hopper 8 is actuated by retracting the shutters 29 and 30 with jack 31 and by modulating energization of electrical magnet 28 in order to pour powder iron into above said alumina crucible. Pouring is stopped when required weight is reached. Shutters 29 and 30 are brought back into their original place in closed position.

Hopper 9 is then vibrated for pouring a required amount of cement into the crucible. If the weighing error is too large, correction is effected in the same manner as in the previous operation for measurement of grain fineness, namely the crucible is picked up again by arm 23 and emptied at position F into the discharge orifice at point 12.

If the weighing result is correct, the crucible is picked up again by arm 23 which goes to position A in registry with a mechanical system 6 which cuts a quartz wool plug and seals the crucible with it in order to prevent projections when the crucible is subsequently heated, while allowing $SO_2$ vapour to escape.

Arm 23 then moves to position G for placing the crucible into the induction furnace 5. Referring to FIG. 8, it will be seen that, in this position G, the arm 23 places the crucible 35 on a tray 36 carried on a stem 37 forming an extension of the piston rod 39 of a jack (not shown), carrying a sealing flange 38.

The furnace itself comprises, in known manner, a bell-shaped quartz enclosure 40 provided with a vacuum connection 41 and surrounded by an inductor coil 42. The lower end 43 of this bell 40 is open downwardly. This bell 40 is held in place by an O-ring 44 resting in a groove of a support member 45. The flange 38 is in turn provided with a groove containing a gasket 46 against which the lower edge 43 of the bell 40 will form a gas-tight joint when the jack is activated and its piston rod 39 raises, lifting the crucible 35 up to the level of inductor coil 42 and then pressing the flange 38 and its gasket 46 against the lower edge 43 of the bell 40, which will thus be hermetically sealed.

The piston rod 39 is further provided with a tube 47 which opens across the flange 38 into the furnace, its other end being connected to a flexible pipe 49.

Referring now to FIG. 3, it will be seen that this flexible pipe 49 is connected to an oxygen source 50 (e.g. a cylinder), the outlet 51 of which is provided with a solenoid valve 52. The outlet 53 of this valve branches out into a first line 54 connected to the flexible line 49 via a flowmeter 56, and a second line 55. This second line is provided with a solenoid valve 57 and joins the flexible line via a second flowmeter 58.

The swivelling arm 23 being in position G places the crucible 35 on the tray 36 of the furnace 5. The jack is then activated for raising the crucible into the furnace bell 40 and sealing the flange 38 against the lower edge 43 of the bell 40. The inductor coil 42 is then switched on and valves 52 and 57 are switched open so that oxygen flows into the furnace and sweeps along $SO_2$ as it is released from the crucible 35. The $SO_2$-laden oxygen stream flows out of the furnace through the upper vacuum connector 41 and through a solenoid valve 59 towards a titration cell 2.

This titration cell 2 may advantageously be of the type described in U.S. patent application (Ser. No. 733,142), filed on May 10, 1985. In the present invention, this cell 2 is formed of a container having a hollow bottom provided with an opening sealed by a remote-controlled draining valve. This container is covered with a lid carrying electrodes connected by lines 61 to a titrator 3. This cell 2 is further connected by a pipe 60 to an automatic burette 1.

The titration cell 2 is filled with a bath in which the $SO_2$-laden oxygen stream is caused to bubble, thus giving rise to a variation of the bath potential, which is constantly corrected by the titrator 3. This titrator 3 controls the automatic burette 1 which will constantly send out to the cell 2 via line 60 the amount of potassium iodate required for keeping constant the bath potential. An automatic read-out from burette 1 indicates the $SO_3$ titration, which is recorded in the programming unit 24. This being completed, the piston rod 39 is lowered and the crucible is picked up again by arm 23, which moves to position F where the crucible is dropped into the waste orifice at point 12.

3. Measurement of limestone filler

This measurement is made by heating a fraction of the cement sample in a platinum crucible placed in the induction furnace 5. In this series of steps, the weight of $CO_2$ released from the cement in the crucible will be measured.

To avoid having several circuits of carrier gas, which would raise problems when switching from one to the other, oxygen is again being used for this measurement. Oxygen is drawn from the above-mentioned source 50 and combined with $CO_2$ released from the cement. The gaseous mixture of $O_2$ and $CO_2$ is passed through a mass of sodium hydroxide granules which pick up the $CO_2$. By weighing this mass before and after the passage of the gaseous mixture, a measurement is obtained of the quantity of $CO_2$ having been picked up, which $CO_2$ was released from the cement.

Figure 5:
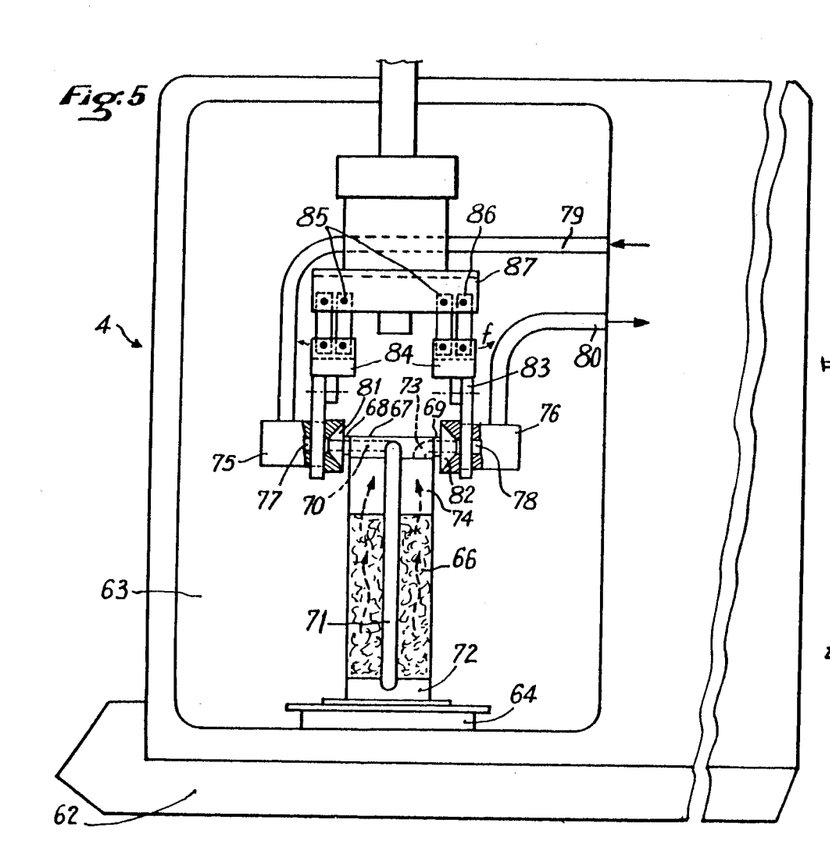
FIG. 5 is a diagrammatic partially cut-out side elevation view of a $CO_2$ trapping and weighing device.

FIG. 5 shows an embodiment of the $CO_2$ measuring device indicated in FIG. 1 with reference number 4. Referring to FIG. 5, there is placed on the tray 64 of an automatic scale 62 a column 65 filled with sodium hydroxide grandules 66. This column is sealed in airtight fashion by a lid 67. This lid carries two diametrically opposed nipples 68 and 69. Inside nipple 68 extends a conduit 70 branching into an external duct 71 which protrudes beyond the lower face of the lid 67 and opens into the base 72 of column 65. Inside nipple 69 extends a conduit 73 which opens into the free space 74 above the mass of sodium granules 66.

To each nipple 68, 69 corresponds a housing 75, 76 across which runs a duct 77, 78 communicating respectively with flexible pipes 79, 80. Pipe 79 will serve to bring into the column 65 the gaseous mixture released upon heating from the crucible in the furnace 5, while pipe 80 is a venting line for releasing out of column 65 the gas from which $CO_2$ will have been extracted.

Each housing 75, 76 presents a conical cup-shaped bearing 81, 82 adapted for respectively mating tightly with the nozzles 68, 69 of the lid 67. The above-mentioned ducts 77, 78 open in the bottom of these cups 81, 82. A ball valve (not shown) may be provided at the junction of ducts 77, 78 with the cups 81, 82 for preventing reverse flow.

Each housing 75, 76 is carried on a lug 83 fixed to a support 84 guided by two parallel arms 85, 86 pivotally connected to a base plate 87 containing a slider mechanism (not shown). This device is designed so that the two deformable parallelograms formed by the arms 85, 86 will spread apart in a symmetrical notion, so that the two housings 75, 76 are in the position shown in FIG. 5, the ball valves are open and the gaseous mixture $O_2$ and $CO_2$ coming from the furnace via line 79 flows through the housing 75 into ducts 70 and 71, and then through the mass 66 of sodium hydroxide granules and is led out of the column 65 via duct 73 and line 80 after $CO_2$ has been trapped in the column.

When the housings 75 and 76 are retracted outwardly, the column 65 rests upon the tray 64 of scale 62, so that a precise weighing of column 65 can then be made.

The two cups 81 and 82 ensure a self-centering of the mating system when lugs 83 carrying the housings 75, 76 press towards each other.

Figure 4:
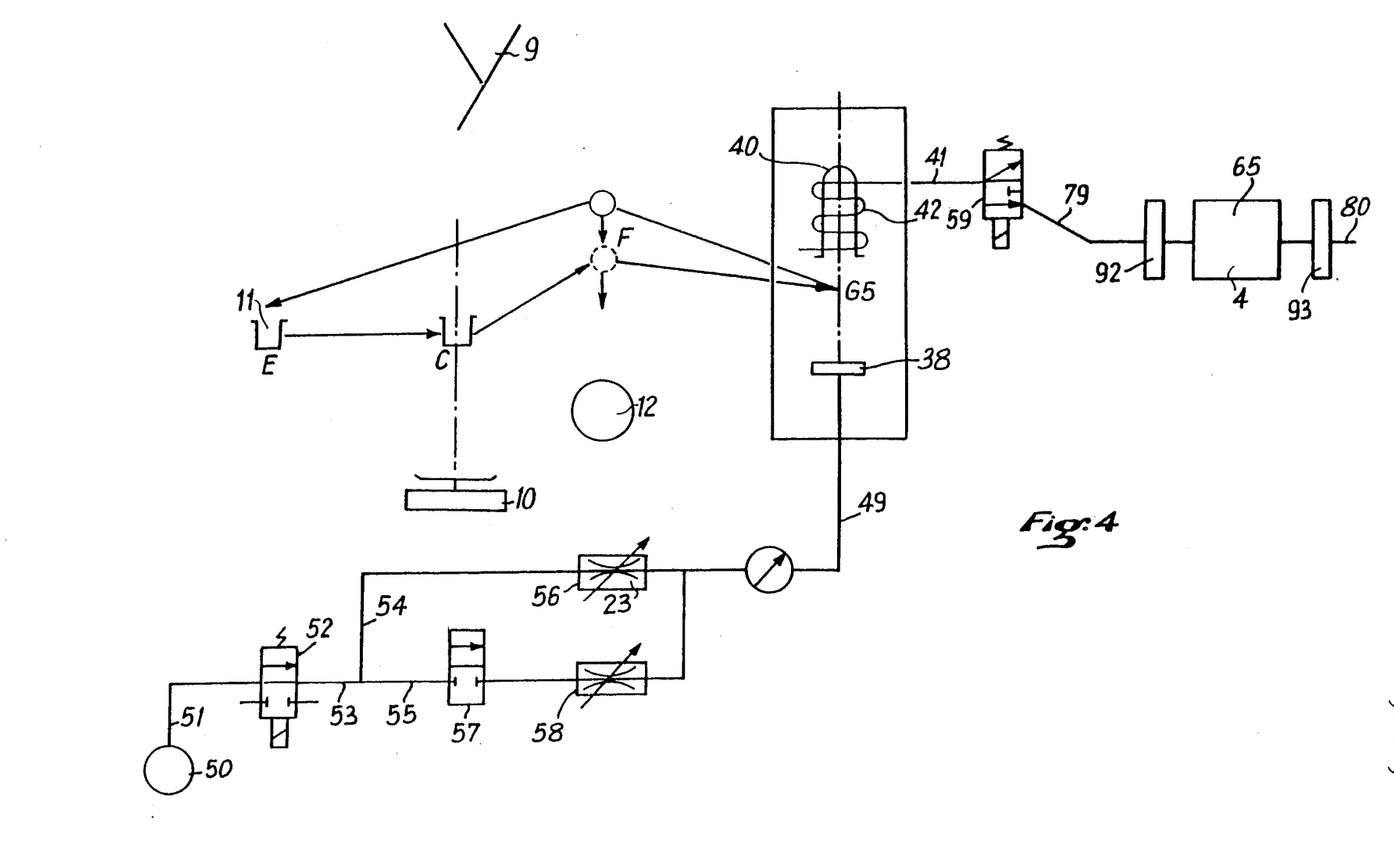
FIG. 4 is a diagram similar to those of FIGS. 2 and 3, showing the sequential steps of the $CO_2$ content measurement.

FIG. 4 shows a diagram of the various steps of the $CO_2$ measuring procedure.

Arm 23 of distribution system I comes into position E for picking up the platinum crucible, which arm 23 had previously taken back to the waiting position at point 11 after having emptied it into the sieve (see above the fineness measurement sequence), and moves on to position C where it lays down this crucible on scale 10 at point 19. Hopper 9 is then activated, as described above, for pouring a set quantity of cement into the crucible. If the weighing is not correct, the crucible will be brought back, as previously described, to the draining orifice at point 12 for being emptied and will then be laid down once more on the scale. If the weighing is correct, arm 23 picks up the crucible again and places it on the tray 38 which will introduce it into the bell 40 of furnace 5 in the same manner as above described for the alumina crucible. Tray 38 will then seal the bell 40 via rod 39.

At that moment, the lugs 83 of the $CO_2$ trapping device shown in FIG. 5 moves apart and column 65 is weighed by the scale 62 which sends out the measured value to the programming unit 24. After this, lugs 83 are moved tightly towards each other and the gas circulation loop is established.

The solenoid valve 52 of the oxygen feed system is open, but valve 57 remains closed, so that the oxygen flow through line 49 is only about half of the flow admitted into the furnace 5 for the previous measurement, namely the $SO_3$ measurement. The $O_2$ and $CO_2$ mixture released from the furnace 5 passes into line 41 and then through the solenoid valve 59 into line 79. Carbon dioxide combines with sodium hydroxide in the column 65. After a set time fixed experimentally for ensuring that $CO_2$ has been completely released from the cement contained in the crucible, the heating system of the furnace 5 is switched off, valve 52 is shut and lugs 83 are moved apart so as to allow column 65 to rest upon the tray of scale 62. A second weighing is made and the result is sent out to the programming unit 24 which determines the weight of the $CO_2$ having been trapped by the sodium hydroxide granules 66. This is done by subtracting the first weighing from the second one. The furnace 5 is then opened and arm 23 picks up the platinum crucible once more for bringing it back to the waiting position at point 11 after having been emptied it into the draining orifice at point 12.

It has however been found that the utilization of a crucible made of platinum or platinum alloy under oxygen flow within an electromagnetic field of about 9 MHz frequency and at about 1,000° C. is not without drawbacks. Indeed, conditions are such that a miniplasma is created, causing a diffusion of platinum which is deposited on the inner wall of the furnace bell 40. This diffusion causes a loss of platinum and disturbs the heating operation of the furnace. To avoid this drawback, a deposit of alumina may be made directly on the platinum.

Since the same oxygen source 50 is used for both the second and third measurements ($SO_3$ and $CO_2$), these measurements cannot be carried out simultaneously and must therefore be made one after the other.

In the example described hereinabove, the $SO_3$ measurement is made first, and then the $CO_2$ measurement, but this sequence may be reversed. On another hand, the fineness measurement which involves a second swivelling arm, namely arm 23 of distribution system II, and mechanical devices which are not utilized for the physio-chemical measurements, may be carried out simultaneously with the other measurements. However, it cannot be made until the initial weighing has been completed using arm 23 of distribution system 1.

Preferably, the $CO_2$ trap 65 will be protected in the manner shown in FIG. 4, namely by a water trap 92 upstream for ensuring that no water or water vapour being released from the cement sample will be trapped by the sodium hydroxide granules 66. The $CO_2$ trap 65 is also protected downstream by a water and $CO_2$ trapping device 93 for avoiding measurements being distorted by atmospheric $CO_2$ and/or water.

When all three above-described cycles are completed, hopper 9 with its spout 9a opening just above the waste discharge orifice P is vibrated for emptying it completely into the orifice. A fresh sample of cement is then loaded into this hopper 9 which is vibrated during sufficient time for allowing a new sample to start flowing down into orifice P. This will ensure that no trace of the previous sample remains in the hopper.

Preferably, when the platinum crucible is at the waiting station at point 11, it will be laid down on a tray carried by a jack which will lower it into a protective well.

We claim:

1. An automatic apparatus for determining certain characteristics of a cement sample such as grain fineness, gypsum content and limestone filler content, comprising
   a furnace,
   a weighing assembly having an automatic scale with at least two feed hoppers,
   a plurality of crucibles,
   a sieve,
   a manipulating assembly for handling said plurality of crucibles and for transporting said crucibles to the vicinity of said furnace, weighing assembly and sieve, said manipulating assembly comprising first and second subassemblies, the first subassembly having a first swiveling arm passing through a plurality of positions located on a first circle, the second subassembly having a second swiveling arm passing through another plurality of positions located on a second circle, the first and the second circles intersecting each other in at least two points, at least one of said points of intersection is located substantially vertically above the automatic scale in said weighing assembly.

2. An apparatus according to claim 1 wherein each said first and second swiveling arm comprises a substantially horizontal member having at an end thereof at least two tongs for grasping said crucibles individually, each said substantially horizontal member being rotatable about its longitudinal axis and fixed to a substantially vertical driving shaft, said first and second swiveling arms being movable along said driving shaft and capable of stopping at a predetermined angular position along said first and second circles, respectively.

3. An apparatus according to claim 2 wherein the second swiveling arm is immobilized in at least eight different positions including
   a first position at which said sieve is dried by drying means,
   an second position at which said sieve is overturned by said second swiveling arm for cleaning said sieve,
   a third position at which fluid pressure means acts on said sieve for carrying out a sieving operation,
   a fourth position at which said sieve is dried by second drying means,
   a fifth position at which said sieve is stored if soiled and a second cleaned sieve is available if needed for replacement,
   a sixth position at which said sieve is cooled and filled by cooling and filling means respectively,
   a seventh position at which said sieve is weighed by said weighing assembly.

4. An apparatus according to claim 3 wherein the furnace comprises a bell-shaped enclosure having a discharge outlet, a plate for introducing the crucible into the furnace, said plate sealing a lower portion of the bell-shaped enclosure when the crucible is positioned within the enclosure, the enclosure being connected to an oxygen source through an oxygen feed circuit, said oxygen feed circuit having a branched feed line and an opening passing through said plate to communicate said enclosure with said branched feed line.

5. An apparatus according to claim 4 wherein the oxygen feed circuit comprises two branch feed lines and means for delivering oxygen to said enclosure at different flow rates in each said line, a first of said branch feed lines having means for measuring oxygen flow for use in measurement of $SO_3$ to determine gypsum content and a second of said branch feed lines having means for measuring oxygen flow for use in measurement of $CO_2$ to determine limestone filler content.

6. An apparatus according to claim 5 further comprising a carbon dioxide trap which comprises a column filled with sodium hydroxide granules, said column is sealed at its upper end by a lid provided with two connecting nipples protruding laterally from said lid at 180° from each other, one said nipple having a first duct which extends to and opens at a base of the column, and the other said nipple having a second duct opened in an upper region of the column.

7. An apparatus according to claim 6 further comprising two symmetrical housings wherein the two nipples respectively cooperate with two symmetrically arranged conical cups facing each other and defined in said two symmetrical housings, wherein one of said two cups is respectively connected through a first one-way valve to a $CO_2$ feed tube and the other of said two cups being connected to a discharge tube through a second one-way valve.

8. Apparatus according to claim 7 wherein the two housings facing each other are carried respectively by two symmetrical lugs, each lug being movably linked with a support through two deformable parallelograms being linked to a driving device adapted for causing the two housings to simultaneously and symmetrically move towards each other or apart from each other, so that when the two housings are close to each other, a gas flow circuit will be established, while when they are drawn apart the gas flow circuit is interrupted and the column may then rest freely on the tray of said automatic scale.

9. An apparatus according to claim 5 wherein said furnace is provided with a branched discharge outlet having at least one line for diverting gases leaving the furnace to a $SO_3$ titration cell and another line for diverting said gases to a $CO_2$ trap.

10. An apparatus according to claim 2 wherein the first swiveling arm is immobilized in at least six different positions including
a first position at which a plug is inserted into said crucibles by first inserting means,
a second position at which said tongs of said first swiveling arm pick up said crucibles,
a third position at which said crucibles are located by said hoppers and weighed by said scale,
a fourth position at which said crucibles are emptied by action of said first swiveling arm to individually invert said crucibles into said sieve,
a fifth position at which said crucibles are emptied by action of said first swiveling arm to individually invert said crucibles into a waste discharge orifice,
a sixth position at which said crucibles are inserted into said furnace by second inserting means.

11. An apparatus according to claim 10 wherein said crucibles are made of alumina.

12. An apparatus according to claim 10 wherein said crucibles are made of platinum.

13. An apparatus according to claim 10 further comprising means for supporting the first hopper substantially above the crucibles resting over said scale, the second hopper including a hopper body and a pouring spout, the second hopper being rotatable for bringing a tip of said spout in a substantially vertical alignment above a weighing area of the scale.

14. An apparatus according to claim 13 in which the first hopper comprises a funnel, a tubular duct, an electro-magnet to stop the flow of powder iron therethrough, and first and second safety shutters, said first shutter being mechanical and said second shutter being magnetic, wherein said shutters are controlled by a single acting jack so that the mechanical shutter is brought below the mouth of said tubular duct while the magnetic shutter is brought on the side of said tubular duct.

15. An apparatus according to claim 13 further comprising a second waste discharge orifice for completely emptying the second hopper when the overall cycle of measurements is completed, wherein said second hopper is vibratory and wherein said second hopper includes a mobile spout capable of rotating about a vertical axis for aligning said spout with said second waste discharge orifice.

* * * * *